(12) United States Patent
Laufer et al.

(10) Patent No.: US 8,710,217 B2
(45) Date of Patent: Apr. 29, 2014

(54) METHOD FOR PRODUCING LACTAMATES BY WAY OF THIN FILM EVAPORATION

(75) Inventors: Wilhelm Laufer, Mannheim (DE); Hans Kasper, Bruehl (DE); Stefan Schattner, Bermersheim (DE); Klaus Allgoewer, Ludwigshafen (DE); Bernd Kray, Speyer (DE); Michael Wuehr, Hirschberg (DE)

(73) Assignee: Rhein Chemie Rheinau GmbH, Mannheim (DE)

( * ) Notice: Subject to any disclaimer, the term of this patent is extended or adjusted under 35 U.S.C. 154(b) by 230 days.

(21) Appl. No.: 12/865,458

(22) PCT Filed: Feb. 5, 2009

(86) PCT No.: PCT/EP2009/051323
§ 371 (c)(1),
(2), (4) Date: Apr. 15, 2011

(87) PCT Pub. No.: WO2009/098259
PCT Pub. Date: Aug. 13, 2009

(65) Prior Publication Data
US 2012/0071648 A1    Mar. 22, 2012

(30) Foreign Application Priority Data
Feb. 8, 2008 (DE) .......................... 10 2008 000 259

(51) Int. Cl.
*C07D 201/14* (2006.01)

(52) U.S. Cl.
USPC ......................................................... 540/612

(58) Field of Classification Search
USPC ......................................................... 540/612
See application file for complete search history.

(56) References Cited

U.S. PATENT DOCUMENTS

| | | | |
|---|---|---|---|
| 3,575,938 A | 4/1971 | Tierney |
| 3,681,293 A | 8/1972 | Jarovitzky |
| 3,793,258 A | 2/1974 | Reinking et al. |
| 4,115,399 A | 9/1978 | Anshus |
| 4,792,540 A | 12/1988 | Bongers et al. |
| 6,013,758 A | 1/2000 | Schmid et al. |

FOREIGN PATENT DOCUMENTS

| | | |
|---|---|---|
| DE | 1204821 B | 11/1965 |
| DE | 1495132 A1 | 1/1969 |
| EP | 0438762 A1 | 7/1991 |
| JP | 07062089 A | 7/1995 |

OTHER PUBLICATIONS

International Search Report from co-pending Application PCT/EP2009/051323 dated Nov. 11, 2009, 5 pages.

*Primary Examiner* — Bruck Kifle
(74) *Attorney, Agent, or Firm* — Nicanor A. Kohncke

(57) ABSTRACT

A method is described for producing lactamates by reacting alcoholates with lactams, wherein a reaction mixture comprising at least one alcoholate and at least one lactam is subjected to thin film evaporation.

13 Claims, 1 Drawing Sheet

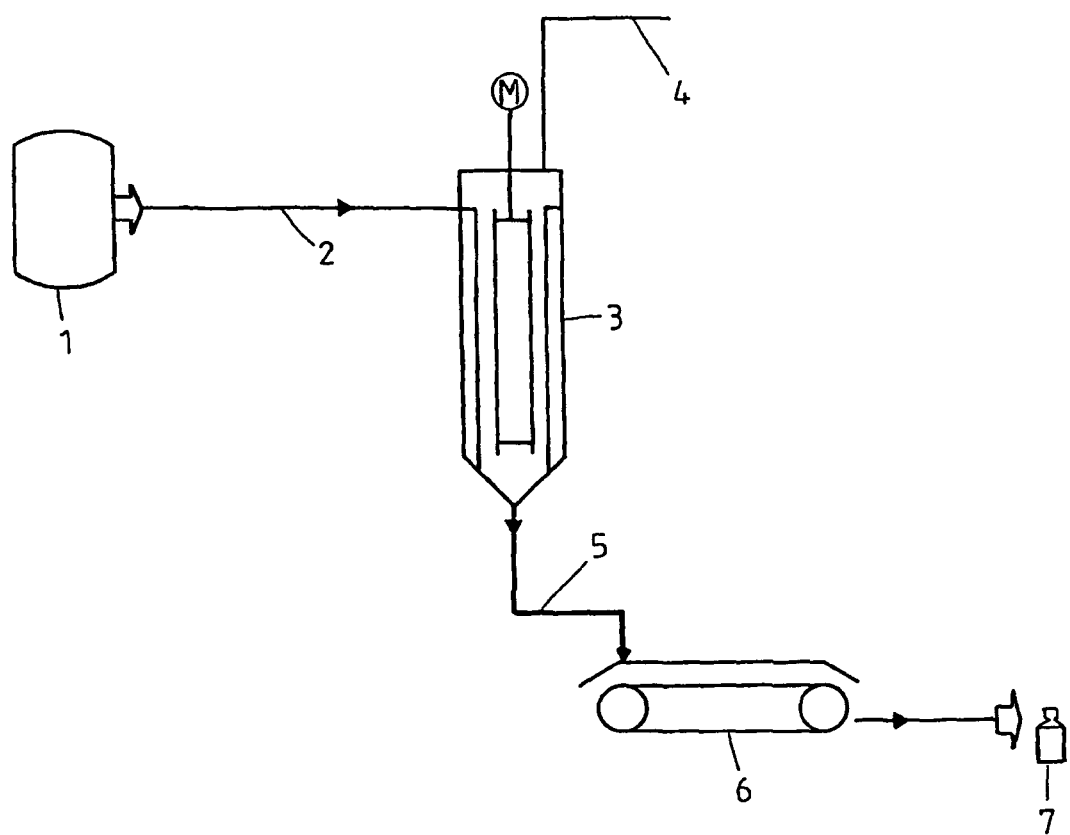

METHOD FOR PRODUCING LACTAMATES BY WAY OF THIN FILM EVAPORATION

CROSS REFERENCE TO RELATED PATENT APPLICATIONS

The present patent application claims the right of priority under 35 U.S.C. §119 (a)-(d) and 35 U.S.C. §365 of International Application No. PCT/EP2009/051323, filed 5 Feb. 2009, which was published in German as International Patent Publication No. WO 2009/098259 A2 on 13 Aug. 2009, which is entitled to the right of priority of German Patent Application No. DE 10 2008 000 259.3 filed on 8 Feb. 2008.

The present invention relates to a process for preparing lactamates by reacting alkoxides with lactams.

When lactams are heated in the presence of alkaline substances, they polymerize to the corresponding polyamides. Suitable and frequently used catalysts for that purpose are lactamates, which are used in combination with isocyanate-based activators.

Processes for preparing lactamate-containing catalyst systems are known per se.

For example, U.S. Pat. No. 4,115,399 describes the preparation of a solution which is suitable for catalysis of the anionic polymerization of 2-pyrrolidinone. The catalyst solution is prepared by batchwise reaction of an alkali metal hydroxide with an excess of 2-pyrrolidinone and subsequent transfer of the resulting mixture to the dehydration at elevated temperature with simultaneous stripping. The reaction is performed in a reaction zone, for example a stirred reactor. After the reaction, the reaction mixture obtained is transferred into a distillation apparatus in which the water formed by the reaction of the alkali metal hydroxide with the excess of 2-pyrrolidinone is removed from the reaction mixture. The process according to U.S. Pat. No. 4,115,399 thus comprises at least two different reaction stages. The reaction of the 2-pyrrolidone and of the alkali metal hydroxide is effected at a temperature between 25 and 100° C., while the distillative workup of the reaction product of 2-pyrrolidinone and the alkali metal hydroxide is effected at 75 to 150° C.

EP 0 438 762 A1 describes a catalyst solution for the anionic polymerization of lactams to polyamide, which, as well as specific modifiers, comprises the lactam to be polymerized, an alkali metal lactamate and 2-pyrrolidinone. The solution to be used for the polymerization is prepared by mixing the lactam and the 2-pyrrolidinone with the individual modifiers and subsequently adding a solid alkali metal alkoxide in a first process step. This mixture is then subsequently subjected to a distillation at elevated temperature and under reduced pressure, in which the alcohol released in the reaction between lactam and alkali metal alkoxide is distilled off.

DE-A 2 035 733 describes the preparation of polyamides by anionic polymerization of lactams, the polymerization being performed in the presence of catalytically active solutions of alkali metal/alkaline earth metal lactamates in α-pyrrolidinone. The batchwise preparation of the catalytically active solution is effected by reacting a lactam with an alcoholic alkali metal/alkaline earth metal alkoxide solution while heating, then adding α-pyrrolidinone and distillatively removing the alcohol formed by the reaction of the lactam with the alkoxide.

U.S. Pat. No. 3,575,938 discloses a process for preparing a catalyst solution for the preparation of polyamides by anionic polymerization. The catalyst solution is prepared by a two-stage process of reacting a metal hydride, metal hydroxide, metal alkylate, metal alkoxide, metal amide or metal carbonate with a lactam monomer at preferably elevated temperature with a subsequent distillation as the second process step.

Further processes for preparing lactamates are known from EP 0 238 143 and DE 12 04 821.

One disadvantage of these processes is the high capital costs, which arise as a result of the specific process apparatus composed of a reactor for the reaction of the lactam with the base and of a distillation apparatus.

Furthermore, the resulting product properties of the catalyst are not always satisfactory. For instance, the preparation processes described may result in turbidity of the catalyst system owing to polymer and oligomer formation, which results in increased purification costs owing to the removal of the oligomers or polymers formed from the apparatus used.

Furthermore, excessively high proportions of oligomers and polymers in the lactamates, which can be used as catalysts for the cast polyamide production, lead more particularly, in the cast polyamide products, to worsened crystallinity of the cast polyamide parts, to a non-constant reactivity and to a restricted storage time of the heated catalyst/caprolactam solution.

Furthermore, high alcohol contents can occur in the resulting catalyst systems as a result of the use of alkoxides as the base, which has an adverse effect on the catalyst suitability and leads to cavity formation in the resulting polyamide products.

A further disadvantage of the processes, which especially work batchwise, is that only low throughputs are achieved. In the continuous processes, it is additionally disadvantageous that large amounts of first runnings are generally required in the distillation to adjust the feed.

Accordingly, it is an object of the present invention to provide a process for preparing catalysts for polymerizing lactams to polyamides, which generally leads to a reduction in the abovementioned problems, more particularly to the avoidance or reduction of formation of polymers or oligomers.

More particularly, the process should preferably enable inexpensive preparation while simultaneously obtaining a high-quality catalyst. The process should lead more particularly to a catalyst system which has a small proportion of oligomer or polymer, such that the customary purification steps are no longer required. Moreover, the resulting catalyst should preferably have a low proportion of alcohol since greater amounts of alcohol lead to a reduced stability of the catalyst, and the presence of alcohol in the anionic polymerization to polyamide leads to gas formation, which can in turn induce formation of cavities in the end product. At the same time, the process should preferably enable high throughputs and preferably ensure rapid attainment of the operating conditions, such that small amounts of first runnings for the feed are required.

The achievement of this object proceeds from a process for preparing lacatamates by reacting at least one alkoxide with at least one lactam.

The process according to the invention is characterized in that a reaction mixture comprising at least one alkoxide and at least one lactam is subjected to a reactive distillation on a thin-film evaporator.

A reactive distillation is understood in the context of the present invention to mean the integration of a reaction (formation of the lactamate catalyst) and of a separation process (distillative removal of the alcohol formed by the reaction).

The reaction mixture used in the process according to the invention comprises at least one lactam. Lactams suitable for this purpose are compounds of the general formula

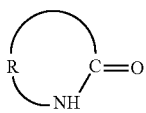

where R is an alkylene group having preferably 3 to 13 carbon atoms, more preferably 5 to 7 carbon atoms. Examples of suitable lactams are caprolactams, especially ε-caprolactam, butyrolactam, enantholactam, caprylolactam, laurolactam, α-pyrrolidinone, piperidone, valerolactam and mixtures thereof. In the context of the present invention, ε-caprolactam is particularly preferred. The lactam used is preferably used in molten form, but it can also be used in flake form.

More particularly, it is preferred that only a single lactam is used in the process according to the invention, which means that a mixture of two or more lactams is not used in the process according to the invention.

Since the lactam used in the process according to the invention rarely reacts quantitatively with the alkoxide to form the lactamate, unconverted lactam is frequently additionally present in the product obtainable by the process according to the invention. According to the selection of the lactam, it may assume a solvent function in the product obtainable by the process according to the invention. In general, the unconverted lactam is not disruptive in the polyamide synthesis, but may lead to side reactions, more particularly to copolyamide formation. Accordingly, it may be preferred in the context of the present invention when the lactam for use in the reaction mixture is coordinated with the lactam to be polymerized later, such that later copolyamide formation can be avoided. In this case, the use of a single lactam in the process according to the invention is preferred.

The alkoxides used for the lactamate formation preferably have a higher basicity than the lactamate anion which is to be formed. Examples of suitable alkoxides are alkali metal or alkaline earth metal alkoxides of low-boiling alcohols, preferably alkali metal or alkaline earth metal methoxides or ethoxides, more preferably sodium methoxide and ethoxide. Examples of further suitable bases are the alkoxides of lithium, potassium, magnesium, calcium, strontium, barium, or else tetraalkylammonium alkoxides.

The alkoxides envisaged can be used in the process according to the invention in pure form as an alkoxide powder, or as a solution or suspension. Suitable solvents for preparing solutions or suspensions are in principle all low-boiling solvents which do not disrupt the reaction. Preference is given to using low-boiling alcohols as solvents for the alkoxides. The alkoxide content in the preferred alcoholic solutions is less than 100% by weight, more preferably 20 to 40% by weight.

In the process according to the invention, the weight ratio of lactam to alkoxide is preferably about 1:1 to 40:1, more preferably about 16:1 to 32:1, especially about 25:2. The ratio selected depends essentially on the melting point of the product which forms. Provided that the melting point is such that it is still possible to work on a thin-film evaporator, it is more particularly also possible to work with a stoichiometric weight ratio between lactam and alkoxide.

The reactive distillation envisaged in accordance with the invention is performed on a thin-film evaporator. A thin-film evaporator is understood in the context of the present invention to mean an apparatus for distillative separation of substance mixtures, the substance mixture to be separated being distributed to give thin layers on hot surfaces by trickling down, the action of centrifugal force or wipers of particular construction. When the liquid to be separated is distributed to thin layers by trickling down, the thin-film evaporator used is frequently also referred to as a falling-film evaporator or trickle column, which can be used in the context of the present invention.

In the present invention, a reaction of the at least one alkoxide with the at least one lactamate to form the catalytically active lactamate takes place on the thin-film evaporator. This reaction releases the corresponding alcohol, which is then withdrawn from the reaction mixture directly on the thin-film evaporator. More particularly, in the context of the present invention, there is no employment of a reaction stage upstream of the reactive distillation, in which there is a reaction of the base with lactam to give the lactamate owing to the temperature selected there.

The thin-film evaporator used in the context of the present process is preferably equipped with a stirrer system.

The process conditions of the thin-film evaporator, especially the selection of temperature and pressure, depend on the lactam used and the alkoxide used and should be adjusted correspondingly.

In the case of use of ε-caprolactam and sodium methoxide or of a methanolic or generally of an alcoholic sodium methoxide solution, the reactive distillation is preferably performed under at least one of the following temperature and/or pressure conditions:

The exact operating conditions of the reactive distillation depend naturally on the lactamate used, more particularly on the melting point thereof. The reactive distillation is preferably performed at an operating temperature of the jacket of the thin-film evaporator of preferably 80 to 180° C., more preferably of 80 to 130° C. The condenser of the thin-film evaporator is operated at a temperature of preferably −10 to 30° C., especially 5 to 15° C. The product temperature in the receiver is preferably 30 to 70° C., more preferably 40 to 60° C., especially 45 to 55° C. This temperature setting in the receiver ensures that there is essentially no reaction of the lactam with the base. The temperature of the reaction line in the connection to the thin-film evaporator can already be adjusted in the direction of the reaction temperature of the reactive distillation. In addition, the reactive distillation is preferably performed such that the product temperature at the outlet is 75 to 120° C., more preferably 80 to 90° C., especially 75 to 85° C. Moreover, the reactive distillation is performed at a contact temperature of preferably 80 to 150° C., more preferably 90 to 100° C. The reactive distillation is preferably performed at a pressure of 50 to 900 mbar, more preferably of 100 to 300 mbar.

The contact times of the reactant mixture employed on the reactive evaporator are generally 2 to 60 sec, more preferably 5 to 20 sec, more preferably 10 to 20 sec.

The reaction mixture composed of alkoxide or alcoholic alkoxide solution and lactam is fed to the thin-film evaporator, preferably at the top.

To remove the alcohol formed during the reaction between lactam and alkoxide, and optionally the solvent alcohol, it has been found to be advantageous when the reaction mixture is additionally subjected to a stripping operation in the thin-film evaporator. In a further preferred embodiment of the process according to the invention, the reaction mixture is therefore stripped with an inert gas during the reactive distillation. Inert gases suitable for that purpose are preferably selected from the group consisting of nitrogen, argon and helium. When a stripping operation is envisaged, it is preferably effected in countercurrent to the flow direction of the reaction mixture. In one embodiment, the stripping gas is supplied to the thin-film evaporator at the bottom and flows counter to the flow of the reaction mixture, which is preferably supplied to the thin-film evaporator at the top.

In the process according to the invention, the product of the reactive distillation is preferably obtained at the bottom of the thin-film evaporator.

When stripping is envisaged during the reactive distillation in the process according to the invention, the stripping is effected with an amount of preferably 0 to 200 m³/h of stripping gas, more preferably 10 to 50 m³/h of stripping gas.

In a further preferred embodiment, the stripping gas is fed in at the bottom of the thin-film evaporator, in the immediate proximity of the lactamate withdrawal point.

For use of the product of the reactive distillation as a catalyst for anionic polymerization of lactams to polyamides, it has been found to be advantageous when the reactive distillation is performed in such a way that the residual content of alcohol in the resulting lactamate-containing product is preferably at most 1% by weight, more preferably at most 0.5% by weight, especially at most 0.3% by weight.

The inventors of the present invention have found that the product obtainable by the process according to the invention, in the turbidity test, exhibits no turbidity in a 10% methanolic solution, which correlates with an at most very low residual content of oligomer and/or polymer.

In addition, it is advantageous for the lactamate-containing product when the residence times thereof during the reactive distillation in the thin-film evaporator are at a minimum This too is achieved by the process according to the invention.

For economic reasons, it is preferred when the throughput of the thin-film evaporator is about 10 to 100 kg/h·m², more preferably about 50 kg/h·m².

In a particularly preferred embodiment, the process according to the invention comprises the following process steps:
(a) providing at least one alcoholic alkoxide solution;
(b) providing at least one lactam;
(c) introducing the at least one lactam into the alcoholic alkoxide solution to obtain a reactant mixture;
(d) homogenizing the reactant mixture obtained in process step (c) at a temperature which is selected such that there is essentially no reaction of the lactam with the alkoxide, to obtain a homogenized reactant mixture;
(e) feeding the homogenized reactant mixture into a thin-film evaporator, preferably via the top of the thin-film evaporator;
(f) reactively distilling the reactant mixture fed in, optionally with simultaneous stripping of the reactant mixture in countercurrent; and
(g) obtaining the lactamate at the bottom of the thin-film evaporator.

When ε-caprolactam and sodium methoxide are used in the process according to the invention, the homogenization envisaged in process step (d) preferably takes place at a temperature of 44 to 50° C. At this temperature, essentially no reaction takes place.

Apparatus for performing the homogenization is known per se to the person skilled in the art. Suitable examples are customary stirred reactors.

The reaction mixture obtained in process step (d) is fed to the thin-film evaporator preferably as soon as the reaction mixture is homogenized. This can be recognized, for example, in that a clear solution is obtained.

During the homogenization in process step (d), preferably essentially no reaction proceeds between the lactam and the alkoxide.

Process step (g) may also be followed by finishing of the lactamate obtained. This is preferably done on a drum flaker or a pelletizing belt, in which case the resulting product is obtained in the form of flakes or pellets.

Since the product of the process according to the invention is oxygen-sensitive, it is preferred when at least individual process steps in the process according to the invention are performed under inert conditions. In a further embodiment of the process according to the invention, however, all process steps, including the finishing if appropriate, are performed under inert conditions, and the resulting, optionally finished product is stored under inert conditions. The performance of the individual process steps under inert conditions is known per se to those skilled in the art. Typically, for this purpose, the devices and apparatuses used are evacuated and then charged with an inert gas, for example nitrogen or argon, until the pressure is equalized again. According to the sensitivity of the resulting lactamate, this operation can be repeated once or more than once.

The process according to the invention can be performed either batchwise or continuously. However, the continuous method is preferred, since this procedure preferably allows constant product features, such as a specific content of sodium caprolactamate, a low residual content of methanol, a better color and a very low polymer content, to be achieved.

It is also possible to add property- and application-related additives, which impair the subsequent lactam polymerization only insignificantly, if at all, to the lactamate obtained. These are, for example, demolding agents, defoamers, heat, light and/or oxidation stabilizers, nucleating agents, tracers, optical brighteners, plasticizers, impact modifiers, fillers and reinforcers, oils, optionally amino-terminated or incorporable polyethers and colorants (pigments).

By virtue of the resulting lactamate-containing product, it is possible to trigger the polymerization of lactams to polyamides directly both in continuous and in batchwise processes. The use of the resulting lactamate-containing product can be used especially in extrusion, injection molding, pultrusion, monomer casting, resin transfer molding, reaction injection molding and rotomolding processes, and to produce composite materials with polyamide as the matrix.

The process according to the invention enables efficient preparation of lactamate-containing catalyst systems, without requiring large amounts of first runnings to establish the feed in the distillation. The formation of polymers and oligomers is minimized and thus enables low cleaning costs of devices and apparatuses used. The resulting product additionally has low residual alcohol concentrations.

The present invention further also relates to the lactamate obtainable by the process according to the invention. This lactamate preferably has an alcohol content of less than 1% by weight, based on the lactamate.

The present invention further provides for the use of the inventive lactamate as a catalyst in polyamide preparation, especially in cast polyamide preparation.

The present invention is described in detail by the working example which follows, which, however, does not constitute any restriction of the invention.

INVENTIVE WORKING EXAMPLE

FIG. 1 shows a process flow diagram for the process according to the invention, which finds use in the process or which follows.

In a vessel (1), a homogenized reactant mixture is prepared from 797 kg of ε-caprolactam and 203 kg of 30% sodium methoxide solution in methanol at a temperature of 47° C. In this homogenized reactant mixture, at first essentially no reaction of the alkoxide with the lactam takes place. Via line (2), the homogenized reaction mixture is transferred into a thin-film evaporator (3) which is operated with the following process parameters:

| Jacket temperature | approx. 120° C. |
|---|---|
| Pressure | 200 mbar |
| Condenser temperature | 10° C. |
| Contact temperature | approx. 110° C. |
| Product temperature at the outlet | approx. 80° C. |
| Product temperature in receiver | approx. 50° C. |
| Nitrogen | approx. 15 to 25 m³/h (countercurrent) |
| Throughput | approx. 50 kg/h · m² |

Under these conditions, the reaction of the lactam with the alkoxide takes place.

At the top of the thin-film evaporator, the methanol is withdrawn as condensate via the pipeline (4). The lactam-containing formed is withdrawn at the bottom of the thin-film evaporator via a pipeline (5) and added to a pelletizing belt or a drum flaker (6). The product (7) is obtained with the following specifications:

Sodium caprolactamate content (determined by acidimetric titration): 17.5 to 19.5%. Methanol content (determined by gas chromatography): <0.3% by weight.

In a solubility test of 2% in caprolactam, a clear solution is obtained at 120° C. A solubility test at room temperature likewise gives a clear solution in 10% methanol.

All process steps are performed under inert atmosphere.

COMPARATIVE EXAMPLE 76 parts by weight of caprolactam and 24 parts by weight of sodium methoxide (as a 30% methanolic solution) are stirred at 80° C. or 110° C. (2 experiments). Thereafter, vacuum (down to 10 mbar) is applied and the excess methanol is distilled off. The distillation time is approx. 2 hours.

The methanol content in the product is above 0.8%.

In a solubility test of 2% in caprolactam, a turbid solution is obtained at 120° C. A solubility test at room temperature in methanol was not carried out since a turbid solution is already obtained when caprolactam is used as the solvent.

The advantages of the processes according to the invention can be summarized as follows:
1. Compared to a batch process in a tank, virtually no oligomers or polymers of the lactam form, which is shown by a comparison of the above-described experiments. This is probably enabled by the fact that the reaction can be performed at higher temperature with a shorter residence time. According to the invention, the proportion of the methanol in the product obtained can be reduced significantly below 1% by weight, preferably below 0.5% by weight.
   The presence of methanol in the polymerization to polyamide leads to gas formation; cavities arise in the polyamide end product, which should be avoided as far as possible.
   Moreover, the lower and constant proportions of methanol can achieve shorter polymerization times overall in the preparation of polyamide.
2. It is additionally found that greater amounts of oligomers are present in the material prepared by the batch process, since the material becomes turbid when melted in caprolactam and is also not completely soluble in alcohols, more particularly in methanol or ethanol. In the batch process in a tank, longer residence times are generally needed owing to the distillation, in order to completely remove the methanol. As a result, however, partial polymerization of the caprolactam already takes place.
   The disadvantages of the presence of oligomers or polymers in the catalyst are firstly that higher costs for cleaning of the apparatuses arise. Secondly, inhomogeneities occur as a result of the high oligomer and polymer content in the polymerization. Since different polymerization rates occur within the polymerization zone, inhomogeneities are formed in the resulting polymer.
   It has surprisingly been possible with the process according to the invention to reduce the proportion of the oligomers of caprolactam which disrupt the polymerization virtually to a proportion which is below the detection limit.
3. In cast polyamide production, the catalyst system obtainable by the process according to the invention can be used, the use of the catalyst system obtained in accordance with the invention leading, in the polyamide castings, to better crystallinity, to a constant reactivity and to achievement of longer storage times of the heated solution of catalyst and caprolactam.
   In addition, the inventive lactamate provides a lactamate catalyst for polyamide preparation which has low variation in the active sodium caprolactamate content. In polyamide preparation using the inventive lactamate as the catalyst, it is therefore possible to use smaller amounts of catalyst and to achieve constant polymerization times.
4. Even known reactive distillation processes for preparing lactamates, as known, for example, from DE 197 15 679 A, do not include any indication that, with the aid of reactive distillation, the formation of oligomeric or polymeric impurities can be reduced or prevented. Nor does DE 197 15 679 A give any indication as to how a lower residual content of alcohol in the lactamate can be achieved. In prior art DE 197 15 679 A, reactive distillation is employed in order to provide a simplified procedure (cf. page 2 lines 29 to 31 of DE 197 15 679 A1). Moreover, the process according to DE 197 15 679 A is performed batchwise in a stirred reactor, which in no way leads to short contact times as achieved in the present application.

The present invention has been described with reference to specific details of particular embodiments thereof. It is not intended that such details be regarded as limitations upon the scope of the invention except insofar as and to the extent that they are included in the accompanying claims.

As used in this specification and the appended claims, the singular forms "a," "an," and "the" include plural referents unless the content clearly dictates otherwise.

What is claimed is:
1. A process for preparing a lactamate, comprising:
   (a) forming a reaction mixture comprising at least one alkoxide and at least one lactam by introducing the at least one lactam to the at least one alkoxide to obtain a reactant mixture wherein said lactam is ε-caprolactam;
   (b) homogenizing the reactant mixture at a temperature between 30° and 70° C. to obtain a homogenized reactant mixture wherein the homogenization results in essentially no reaction between the at least one alkoxide with the at least one lactam;
   (c) feeding the homogenized reactant mixture into a thin-film evaporator;

(d) reactively distilling the reactant mixture fed in the thin-film evaporator at a temperature of 30 to 60° C., optionally with simultaneous stripping of the reactant mixture in countercurrent; and
(e) obtaining the lactamate in the thin-film evaporator.

2. The process as claimed in claim 1, wherein the process is performed continuously.

3. The process as claimed in claim 1, wherein the reactive distillation is performed in a falling-film evaporator.

4. The process as claimed in claim 1, wherein the alkoxide is an alkali metal alkoxide, alkaline earth metal alkoxide or tetraalkylammonium alkoxide.

5. The process as claimed in claim 1, wherein the weight ratio of the lactam to the alkoxide in the reaction mixture is 1:1 to 40:1.

6. The process as claimed in claim 1, further comprising:
subjecting the reaction mixture to a stripping operation during the reactive distillation.

7. The process as claimed in claim 6, wherein the stripping operation is effected in countercurrent to the flow of the reaction mixture.

8. The process as claimed in claim 1, further comprising:
finishing the lactamate obtained on a drum flaker or a pelletizing belt.

9. The process as claimed in claim 1, wherein the process is performed under inert conditions.

10. The process according to claim 1, wherein the thin-film evaporator further comprises a jacket having an operating temperature from 80 to 180° C.

11. The process according to claim 1, wherein the thin-film evaporator further comprises a condenser having a temperature from −10° C. to 30° C.

12. The process according to claim 1, wherein the thin-film evaporator has a pressure of 50 to 900 mbar.

13. The process according to claim 1, wherein the reactive distillation is via a trickle column.

* * * * *